US012799065B2

(12) United States Patent
Orlovic et al.

(10) Patent No.: US 12,799,065 B2
(45) Date of Patent: Nov. 17, 2026

(54) CO-CRYSTAL OF CITRIC ACID AND GLYCINE AND USES THEREOF

(71) Applicant: Purac Biochem B.V., Gorinchem (NL)

(72) Inventors: Marija Orlovic, Gorinchem (NL); Cynthia Berenice Marmolejo, Gorinchem (NL); Jan Van Krieken, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 455 days.

(21) Appl. No.: 18/639,565

(22) Filed: Apr. 18, 2024

(65) Prior Publication Data

US 2024/0262779 A1 Aug. 8, 2024

Related U.S. Application Data

(63) Continuation of application No. PCT/EP2022/078737, filed on Oct. 14, 2022.

(30) Foreign Application Priority Data

Oct. 20, 2021 (EP) .................................... 21203662

(51) Int. Cl.

| | |
|---|---|
| ***C07C 59/265*** | (2006.01) |
| ***A23G 3/36*** | (2006.01) |
| ***A23L 27/00*** | (2016.01) |
| ***A23L 27/20*** | (2016.01) |
| ***A23L 27/21*** | (2016.01) |
| ***C07C 229/08*** | (2006.01) |

(52) U.S. Cl.

CPC .............. *C07C 59/265* (2013.01); *A23G 3/36* (2013.01); *A23L 27/00* (2016.08); *A23L 27/2028* (2016.08); *A23L 27/21* (2016.08); *A23L 27/88* (2016.08); *C07C 229/08* (2013.01); *A23V 2002/00* (2013.01); *C07B 2200/13* (2013.01)

(58) Field of Classification Search

None

See application file for complete search history.

(56) References Cited

U.S. PATENT DOCUMENTS

| | | | |
|---|---|---|---|
| 3,558,325 | A | 1/1971 | Recsei |
| 2018/0228753 | A1 | 8/2018 | Tsai et al. |

FOREIGN PATENT DOCUMENTS

| | | | |
|---|---|---|---|
| EP | 1 504 675 | A1 | 2/2005 |
| JP | 2018-157788 | A | 10/2018 |
| WO | WO-02/36543 | A1 | 5/2002 |

(Continued)

OTHER PUBLICATIONS

International Search Report and Written Opinion issued in connection with PCT International Patent Application No. PCT/EP2022/078737 dated Feb. 10, 2023 (8 pages).

(Continued)

*Primary Examiner* — Medhanit W Bahta

(74) *Attorney, Agent, or Firm* — Sunit Talapatra; Foley & Lardner LLP

(57) ABSTRACT

A co-crystal of citric acid and glycine containing citric acid and glycine in a molar ratio of 1:3 is disclosed. It was unexpectedly discovered that this co-crystal of citric acid and glycine can suitably be produced in the form of powders that exhibit very low hygroscopicity and that are capable of imparting a sour flavour that is very similar to that of citric acid. Also disclosed are processes that enable the preparation of the co-crystal in high yield.

14 Claims, 3 Drawing Sheets

500 µm

(56) References Cited

FOREIGN PATENT DOCUMENTS

| | | | |
|---|---|---|---|
| WO | WO-2020/260194 | A1 | 12/2020 |
| WO | WO-2021/126549 | A1 | 6/2021 |

OTHER PUBLICATIONS

Losev et al., "Selective Effect of Carboxylic Acids on Glycine Polymorphisms and Cocrystal Formation", Doklady Physical Chemistry, Kluwer Academic Publishers-Plenum Publishers, NE, vol. 439, No. 2, XP019947314, Sep. 4, 2011, pp. 153-156.

CO-CRYSTAL OF CITRIC ACID AND GLYCINE AND USES THEREOF

TECHNICAL FIELD OF THE INVENTION

The invention relates to a co-crystal of citric acid and glycine and to a process of preparing such a co-crystal. The co-crystal of the present invention contains citric acid and glycine in a molar ratio of 1:3.

The invention further relates to a particulate composition comprising particles that contain at least 5 wt. % of the aforementioned co-crystal and to the application of such a composition as a food ingredient in edible products, e.g. for sanding candies.

BACKGROUND OF THE INVENTION

It is well-known to coat sugar confectionery with a blend of sugar and acid powders (called 'acid sanding'). Use of powdered citric acid in acid sanding is associated with stability problems that arise from the fact that citric acid is hygroscopic. Citric acid powder attracts significant moisture from its surroundings. This process has an adverse impact on the appearance of the coated confectionery product, but also on its taste and texture.

U.S. Pat. No. 3,558,325 describes a method of improving the taste, smoothness, mellowness and flavour of alcoholic beverages by incorporating in said beverage between 0.01% and 6.0% of a non-toxic palatably acceptable salt formed by reacting alpha-alanine or glycine with acids selected from the group consisting of ascorbic, malic, gluconic, citric, tartaric and cyclamic. Example I describes the preparation of a glycine-citrate by dissolving 1.9 grams of citric acid in 3 cc. hot water, followed by gradual addition of 0.75 gram of glycine until all the components were dissolved. A small amount of activated carbon was added and the solution was filtered under suction. The filtrate was cleared, followed by addition of methanol and isopropanol in small quantities until a turbidity occurred. The salt was crystallized by cooling. The salt was recrystallized in water. The glycine-citrate so obtained melted at 168-169° C. and had the empirical formula $C_8H_{13}NO_9$.

Losev et al. (*Selective Effect of Carboxylic Acids on Glycine Polymorphisms and Cocrystal Formation*, Doklady Physical Chemistry, 2011, Vol. 439, Part 2, pp. 153-156.) describe a study in which the effects of carboxylic acid additions on crystallisation of alpha-glycine in experiments on co-crystallisation and joint mechanical treatment was investigated. Formation of 1:1 cocrystals stoichiometric acid amounts was not observed during crystallisation from aqueous solution of crystallisation upon mechanical treatment.

US 2018/0228753 describes co-crystals of a substituted glycine compound and a co-former (e.g. tartaric acid or fumaric acid).

WO 2020/260194 describes a particulate composition comprising at least 1 wt. % of malate particles, said malate particles having a diameter of 50 to 1000 μm and comprising at least 70 wt. % of co-crystal of malic acid and alkali metal hydrogen malate. These particulate compositions may be used in for acid sanding of confectionery.

SUMMARY OF THE INVENTION

The inventors have unexpectedly discovered a co-crystal of citric acid and glycine that can suitably be produced in the form of powders that exhibit very low hygroscopicity and that are capable of imparting a sour flavour that is very similar to that of citric acid.

Thus, a first aspect of the invention relates to a co-crystal of citric acid and glycine, said co-crystal containing citric acid and glycine in a molar ratio of 1:3.

Although the inventors do not wish to be bound by theory, it is believed that when particles of the co-crystal of the present invention come into contact with saliva the co-crystal instantly dissociates to citric acid and glycine. Thus, the flavour of citric acid is immediately released within the mouth upon consumption of edible products that have been coated with particles of the co-crystal.

A second aspect of the invention relates to a particulate composition comprising citric acid/glycine co-crystal particles containing at least 5 wt. % of the aforementioned co-crystal.

A third aspect of the invention relates to a process of preparing co-crystal particles comprising co-crystal of citric acid and glycine, said process comprising:

- providing seed crystal particles containing at least 50 wt. % of crystalline material comprising an organic acid;
- providing an aqueous solution containing citric acid and glycine in a molar ratio of 0.25 to 0.40;
- spraying the aqueous solution onto the seed crystal particles to produce loaded particles;
- removing water from the loaded particles.

A fourth aspect of the invention relates to an alternative process of preparing co-crystal particles comprising co-crystal of citric acid and glycine, said process comprising:

- providing an aqueous mixture containing citric acid and glycine in a molar ratio of 0.25 to 0.40, said mixture comprising 1-40 wt. % of water;
- crystallising co-crystal of citric acid and glycine; and
- drying the crystallised co-crystal.

The aforementioned processes of preparing co-crystal particles offer the advantage that the co-crystal can be produced in high yield. If citric acid and glycine are applied in a molar ratio of 1:3, a yield close to 100% can be realised.

A fifth aspect of the invention relates to the use of particles containing at least 5 wt. % of the co-crystal of the present invention as a food ingredient.

A sixth aspect of the invention relates to a method of preparing an edible product, said method comprising combining the particulate composition of the present invention with one or more other food ingredients.

A seventh aspect of the invention relates to an edible product containing at least 0.05 wt. % of co-crystal particles containing at least 5 wt. % of the co-crystal of the present invention.

DETAILED DESCRIPTION OF THE INVENTION

An aspect of the present invention relates to a co-crystal of citric acid and glycine, said co-crystal containing citric acid and glycine in a molar ratio of 1:3.

The term "co-crystal" as used herein refers to a crystalline single phase material composed of two or more different molecular or ionic compounds in a stoichiometric ratio, which are neither solvates nor simple salts.

According to a preferred embodiment, the co-crystal of the present invention shows an endothermic peak at a temperature of 130-200 °C, more preferably at a temperature of 140-190 °C, having an enthalpy of at least 110 J/g, more preferably of at least 110 J/g, even more preferably of at least 120 J/g, most preferably of at least 140 J/g, as determined by means of differential scanning calorimetry. Preferably, the enthalpy of the endothermic peak does not exceed 195 J/g, more preferably it does not exceed 190 J/g. Even more preferably, the co-crystal shows an endothermic peak at a temperature of 150-180 °C, most preferably at a temperature of 155-170 °C, having an enthalpy of at least 120 J/g, more preferably of at least 130 J/g, most preferably of at least 150 J/g, as determined by means of differential scanning calorimetry. Preferably, the enthalpy of the endothermic peak in the recited temperature range does not exceed 190 J/g, more preferably it does not exceed 180 J/g.

Another aspect of the invention relates to a particulate composition comprising citric acid/glycine co-crystal particles containing at least 5 wt. % of the co-crystal of the present invention. The co-crystal particles preferably contain at least 40 wt. %, more preferably at least 70 wt. % and most preferably at least 80 wt. % of the co-crystal.

Besides citric acid/glycine co-crystal particles the particulate composition of the present invention may comprise other particulate components, such as sugar, salt or acid powders. Preferred acid powders are powders based on malic acid such as PURAC® Powder MA or PURAC® Powder MAX. The term "malic acid" as used herein, unless indicated otherwise, also encompasses edible salts of malic acid.

According to a preferred embodiment, the co-crystal particles in the particulate composition contain at least 50 wt. %, more preferably at least 70 wt. %, more preferably at least 85 wt. % and most preferably at least 90 wt. % of the co-crystal of citric acid and glycine.

The particulate composition preferably contains at least 1 wt. % of the co-crystal particles.

In one embodiment of the invention, the co-crystal particles represent the bulk of the particulate composition. Accordingly, such particulate composition preferably comprises at least 50 wt. %, more preferably at least 75 wt. %, most preferably at least 90 wt. % of the co-crystal particles.

In another embodiment, the particulate composition contains a combination of the co-crystal particles and sugar particles. Such a blend can suitably be used for acid sanding of confectionery. Accordingly, such particulate composition preferably comprises 1-95 wt. % of the co-crystal particles and 5-99 wt. % of sugar particles, more preferably 2-50 wt. % of the co-crystal particles and 50-98 wt. % of sugar particles. Even more preferably, the particulate composition comprises 3-30 wt. % of the co-crystal particles and 60-97 wt. % of sugar particles. Preferably, the combination of co-crystal particles and sugar constitutes at least 40 wt. %, more preferably at least at least 60 wt. % and most preferably at least 80 wt. % of the particulate composition.

In yet another embodiment, the particulate composition contains a combination of the co-crystal particles and particles comprising malic acid. Such a blend can suitably be used for acid sanding of confectionery. Accordingly, such particulate composition preferably comprises 10-90 wt. % of the co-crystal particles and 10-90 wt. % of particles containing at least 20 wt. % of malic acid, more preferably 20-80 wt. % of the co-crystal particles and 20-80 wt. % of particles containing at least 20 wt. % of malic acid. Even more preferably, the particulate composition comprises 30-70 wt. % of the co-crystal particles and 30-70 wt. % of particles containing at least 20 wt. % of malic acid.

The water content of the co-crystal particles typically does not exceed 5 wt. %, more preferably the water content does not exceed 3 wt. %.

The particulate composition of the present invention preferably has a volume weighted average diameter $D_{4,3}$ of 50-1,200 μm, more preferably of 300-1,100 μm.

According to another preferred embodiment, the particles of the particulate composition have the following particle size distribution:

$$D_{10} \geq 10\,\mu m;$$

$$50\,\mu m \leq D_{50} \leq 1{,}000\,\mu m;$$

$$D_{90} \leq 1{,}600\,\mu m;$$

wherein the vol. % of particles with diameters smaller than Dx equals x vol. % and wherein the vol. % of particles with diameters larger than Dx equals (100–x) vol. %.

The particle size distribution of the particulate composition can suitably be determined by means of laser diffraction using a Mastersizer 3000, ex Malvern Panalytical as described in the Examples.

Another aspect of the invention relates to a process of preparing co-crystal particles comprising co-crystal of citric acid and glycine, said process comprising:

- providing seed crystal particles containing at least 50 wt. % of crystalline material comprising an organic acid, preferably selected from citric acid, malic acid, lactic acid, acetic acid, fumaric acid, adipic acid, tartaric acid and combinations thereof;
- providing an aqueous solution containing citric acid and glycine in a molar ratio of 0.25 to 0.40;
- spraying the aqueous solution onto the seed crystal particles to produce loaded particles;
- removing water from the loaded particles.

Preferably, the seed crystal particles contain at least 30 wt. % of the organic acid selected from citric acid, malic acid, lactic acid, acetic acid, fumaric acid, adipic acid, tartaric acid and combinations thereof In accordance with a particularly preferred embodiment, the seed crystal particles contain at least 50 wt. %, more preferably at least 70 wt. % and most preferably at least 90 wt. % of the co-crystal of citric acid and glycine as described herein before.

The aqueous solution that is employed in the present process preferably contains citric acid and glycine in a molar ratio of 0.28-0.37, more preferably in a molar ratio of 0.30-0.35 and most preferably in a molar ratio of 0.32-0.34.

The aqueous solution containing citric acid and glycine that is used in the present process preferably contains not more than 30 wt. %, more preferably not more than 15 wt. %, even more preferably not more than 5 wt. % and most preferably no organic solvent (e.g. methanol, ethanol or isopropanol).

The aqueous solution containing citric acid and glycine preferably contains at least 30 wt. %, more preferably 35-55 wt. % and most preferably 40-50 wt. % of the combination of citric acid and glycine.

Preferably water is removed from the loaded particles by exposing the particles to a gas flow having a temperature of at least 50 °C, more preferably a temperature of 60-150 °C before it comes into contact with the loaded particles. The gas flow preferably contains at least 90 vol. % of air.

Water may suitably be removed from the loaded particles in a fluidized bed dryer. The bed temperature of the fluidised loaded particles is preferably kept at 40-98 °C. The inlet temperature of the gas that is used to remove water from the fluidised loaded particles in the fluidized bed dryer is preferably in the range of 70-180 °C.

The present process may advantageously be carried out in a fluid bed granulator or in a spray drier. In case of a spray drier, the seed crystal particles and the aqueous solution are concurrently introduced into the spray dryer. Seed crystal particles can be obtained from the fines of the dried product (recycle).

In case of a fluid bed granulator, first a fluidised bed of seed crystal particles is formed. Subsequently, the aqueous solution is sprayed onto the seed crystal particles to produce loaded particles and simultaneous a gas flow is passed through the fluidised bed to remove water from the loaded particles.

According to a particularly preferred embodiment, the present process yields citric acid/glycine co-crystal particles as defined herein before.

Yet another aspect of the invention relates to an alternative process of preparing co-crystal particles comprising co-crystal of citric acid and glycine, said process comprising:

- providing an aqueous mixture containing citric acid and glycine in a molar ratio of 0.25 to 0.40, said mixture comprising 1-40 wt. % of water;
- crystallising co-crystal of citric acid and glycine; and
- drying the crystallised co-crystal.

The water content of the aqueous mixture as mentioned herein refers to the total water content including any water that is contained in hydrates, such as citric acid monohydrate.

The aqueous mixture employed in this process can be an aqueous solution that, prior to the precipitation step, comprises fully dissolved citric acid and fully dissolved glycine. Precipitation of co-crystal from this solution may be induced, for instance, by adding seeding crystals, cooling and/or dehydration.

In accordance with an alternative embodiment, the aqueous mixture comprises undissolved glycine and/or undissolved citric acid. The inventors have unexpectedly discovered that if water is added to a mixture containing citric acid and glycine in a molar ratio of 0.25 to 0.40, co-crystal of citric acid and glycine will be formed.

The amount of water present in the aqueous mixture preferably is in the range of 1 to 40 wt. %, more preferably of 2 to 25 wt. %, even more preferably 3 to 15 wt. % and most preferably 5 to 10 wt. %.

Preferably, the precipitation of co-crystal of citric acid and glycine is carried out a temperature in the range of 10 to 95 °C, more preferably 20 to 90 °C. and most preferably 30 to 80 °C.

The aqueous mixture that is employed in the present process preferably contains citric acid and glycine in a molar ratio of 0.28-0.37, more preferably in a molar ratio of 0.30-0.35 and most preferably in a molar ratio of 0.32-0.34.

The aqueous mixture containing citric acid and glycine that is used in the present process preferably contains not more than 15 wt. %, more preferably not more than 5 wt. %, even more preferably not more than 2 wt. % and most preferably no organic solvent (e.g. methanol, ethanol or isopropanol).

The aqueous mixture containing citric acid and glycine preferably contains at least 60 wt. %, more preferably 75-98 wt. % and most preferably 90-95 wt. % of the combination of citric acid and glycine.

In a preferred embodiment, the recovered co-crystal is subjected to a drying step to reduce the water content to less than 5 wt. %, more preferably less than 2 wt. % and most preferably less than 1 wt. %.

According to a further preferred embodiment, the recovered co-crystal or the dried recovered co-crystal is subject to a size reduction step, such as grinding or milling. Classification of the size reduced co-crystal particles, e.g. by sieving, may be used to achieve a more uniform particle size.

According to a particularly preferred embodiment, the present process yields citric acid/glycine co-crystal particles as defined herein before.

A further aspect of the invention relates to the use of particles containing at least 5 wt. %, more preferably at least 50 wt. % and most preferably at least 80 wt. % of a co-crystal of citric acid and glycine as defined herein before as a food ingredient.

Preferably, the present use comprises application of the co-crystal particles in or onto an edible product having a water content of less than 30 wt. %, more preferably of less than 15 wt. % and most preferably less than 15 wt. %.

According to a preferred embodiment, the use comprises application of the co-crystal in or onto a confectionery product.

According to a particularly preferred embodiment, the use comprises application of the co-crystal particles as a coating onto the surface of an edible product, such as a confectionery product.

Another aspect of the invention relates to a method of preparing an edible product, said method comprising combining a particulate composition as described herein before with one or more other food ingredients. Preferably, the combining of the particulate composition with the one or more other food ingredients is not accompanied by dissolution of the co-crystal.

In one embodiment, the present method comprises combining the particulate composition with sugar. In this embodiment, the particulate composition preferably contains at least 20 wt. %, more preferably at least 30 wt. % of the co-crystal particles, most preferably at least 50 wt. % of the co-crystal particles. By mixing the particulate composition with sugar a coating composition may be prepared that can suitably be used for acid sanding of confectionery products.

In another embodiment, the present method comprises application of the particulate composition onto the surface of an edible product, such as a confectionery product. In this embodiment, the particulate composition preferably comprises 1-95 wt. % of the co-crystal particles and 5-99 wt. % of sugar particles, more preferably 2-50 wt. % of the co-crystal particles and 50-98 wt. % sugar particles.

In another preferred embodiment, the particulate composition comprises 10-90 wt. % of the co-crystal particles and 10-90 wt. % of particles comprising at least 20 wt. % of malic acid, more preferably 20-80 wt. % of the co-crystal particles and 20-80 wt. % particles comprising at least 20 wt. % of malic acid.

Yet another aspect of the invention relates to an edible product containing at least 0.05 wt. %, more preferably 0.15-30 wt. % of co-crystal particles containing at least 5 wt. % of a co-crystal of citric acid and glycine as described herein before.

The water content of the edible product in which the co-crystal particles of the present invention are applied, preferably is less than 30 wt. %, more preferably less than 15 wt. % and most preferably less than 15 wt. %.

Preferably, besides the co-crystal particles, the edible product contains at least 0.05 wt. %, more preferably 0.15-30 wt. % of particles comprising at least 20 wt. % malic acid.

According to a particularly preferred embodiment, the edible product is coated with the co-crystal particles. More preferably, the edible product is coated with a mixture of the co-crystal particles and sugar particles. Even more preferably, the edible product is coated with a particulate composition containing the co-crystal particles and sugar particles as described above.

The edible product of the present invention preferably is a confectionery product, more particularly a soft candy.

The invention is further illustrated by the following non-limiting examples.

EXAMPLES

Example 1

A glass bottle of 100 ml was charged with 21.11 g of citric acid monohydrate food grade (0.10 mol) and 22.72 g of glycine (0.30 mol). The powders were mixed by shaking the flask. Water (2.63 g) was added to the bottle, and the mixture so obtained was stored at 40 °C. After two hours the thick slurry had turned into a white solid mass.

The next day a part of the solid mass (11.02 g) was dried at room temperature under vacuum (p<10 mbara) for one night. The dried product had a water content of 0.4 wt. %. The dried product was analysed by differential scanning calorimetry (Q2000, ex TA Instruments) and dynamic vapour sorption (DVS).

Figure 1A:
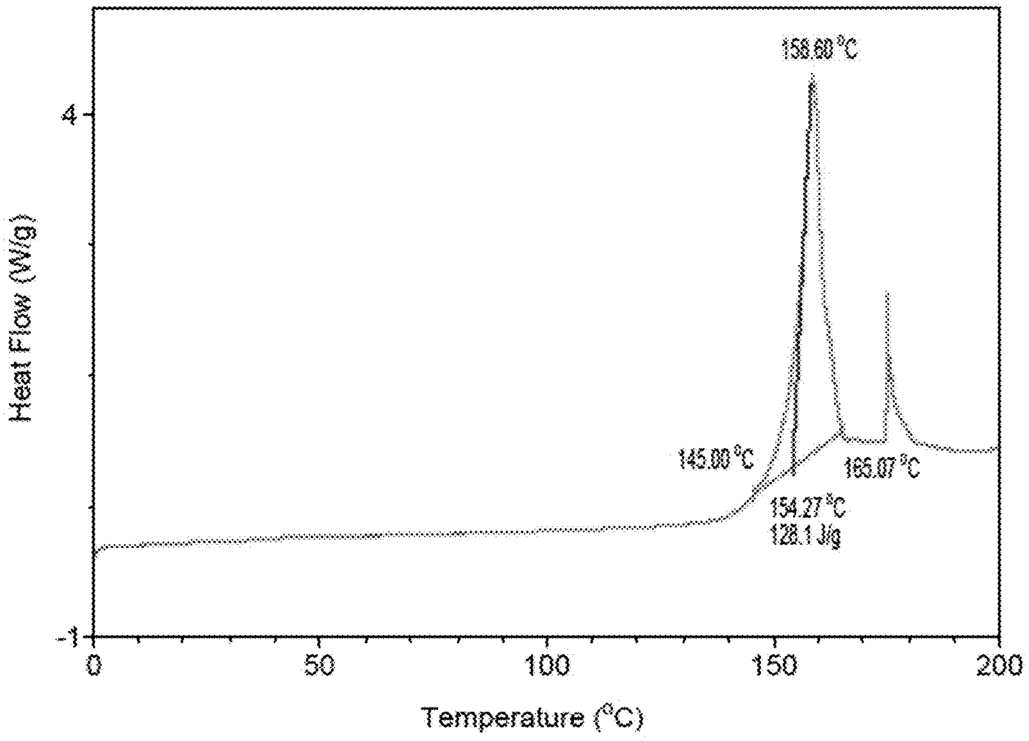
FIG. 1A and FIG. 1B show the DSC curve so obtained by Example 1 (FIG. 1A) and the DVS graph so obtained by Example 1 (FIG. 1B), respectively.
Figure 1B:
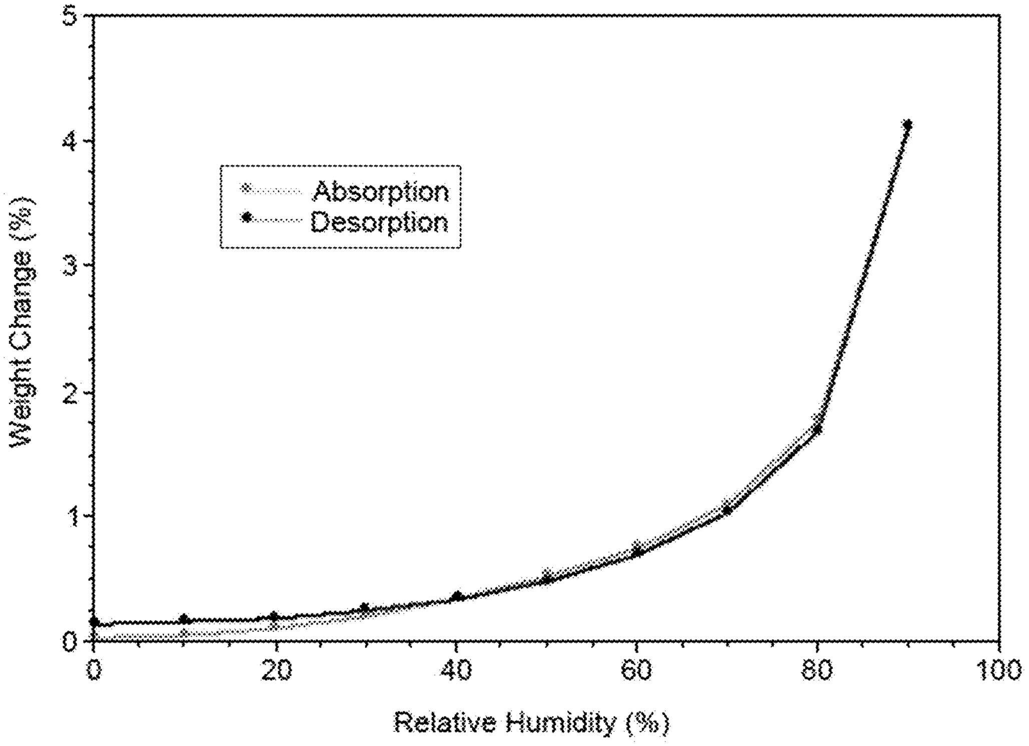

The DSC curve so obtained is shown in FIG. 1*a*. The DVS graph so obtained is shown in FIG. 1*b*.

The enthalpy of 128.1 J/g and the temperature of the endothermic peak of 158.6 °C observed in the DSC curve are somewhat lower than those observed in some of the experiments described below. This may be caused by incomplete conversion of the starting materials into the 1:3 co-crystal.

The DVS graph shows that moisture uptake at 80% RH was about 2-3 wt. %, which is considerably lower than the moisture uptake of citric acid monohydrate at 80% RH (about 20 wt. %).

Example 2

Approximately 4,255 grams of aqueous solution containing citric acid and glycine in a molar ratio of 1:3 was prepared on the basis of the recipe that is shown in Table 1.

TABLE 1

| | Wt. % |
|---|---|
| Glycine, Sigma-Aldrich, Food Grade | 25.36 |
| Citric acid anhydrous, RFI 30-100 mesh | 21.64 |
| Demi water | 53.00 |

Demi water was weighed into a 5 L glass beaker equipped with magnetic stirrer. The powders were added gradually upon stirring. The solution was heated to 40 °C to dissolve the powders. Once the powders had dissolved, the solution was allowed to cool down to room temperature.

Next 0.3 g of co-crystal of citric acid and glycine (1:3 mol/mol) was added and the solution was left overnight to crystallize. The next day, the solution had turned into white paste. Solid liquid separation by means of centrifugation was performed to remove the mother liquor (centrifuge: 10 mins, 3000 rpm, HERMLE Sieva-2 (X-6449)), 25 μm—filter cloth). The solids collected were placed onto several metal trays to dry the remaining liquid in vacuum oven (at 20 °C).

After 2 days the crystals had a moisture content of approximately 7.5 wt. %. The solids were further dried in a vacuum oven at 30 °C for 5 hours to reduce the moisture content to 5 wt. %. A food processor was used to convert the resulting cake into a powder.

Figure 2:
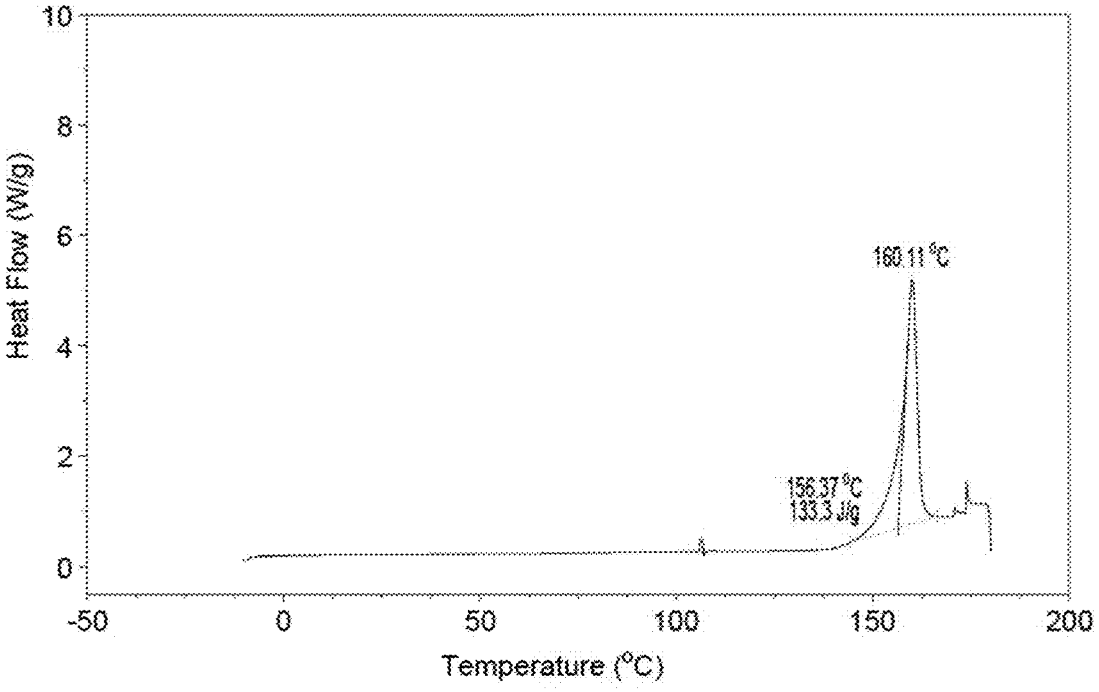
FIG. 2 shows the DSC curve so obtained by Example 2 of the present invention.

A sample of the powder was analysed by means of differential scanning calorimetry (Q2000, ex TA Instruments). The sample was heated from −10 °C to 200 °C at a rate of 10 °C/min. The DSC curve so obtained is shown in FIG. 2.

Example 3

Approximately 7450 grams of an aqueous solution of citric acid and glycine (spraying solution) having the same composition as the solution of Example 2 was prepared in the same way as in Example 2.

A granulation trial was performed in a fluid bed granulator (Procell LabSystem) in which the spraying solution was sprayed onto the fluidized powder of Example 2. The operating conditions of the granulator are summarized in Table 2.

TABLE 2

| Parameters | |
|---|---|
| Air flow [$m^3$/h] (s.p.) | 100-130 |
| $T_{inlet}$ air [° C.] (s.p.) | 100-130 |
| De-humidifier | ON |
| $T_{bed}$ [° C.] | 60-65 |
| Spray liquid T [° C.] | 40 |
| Atomization air pressure [bar] | 3 |
| Liquid pump # | 2 up to 8.5 |
| Spray rate [g/min] | 26 up to ~100 |
| Starting material [g] | 805 |
| Total liquid sprayed [g] | 5280 |

Figure 3:
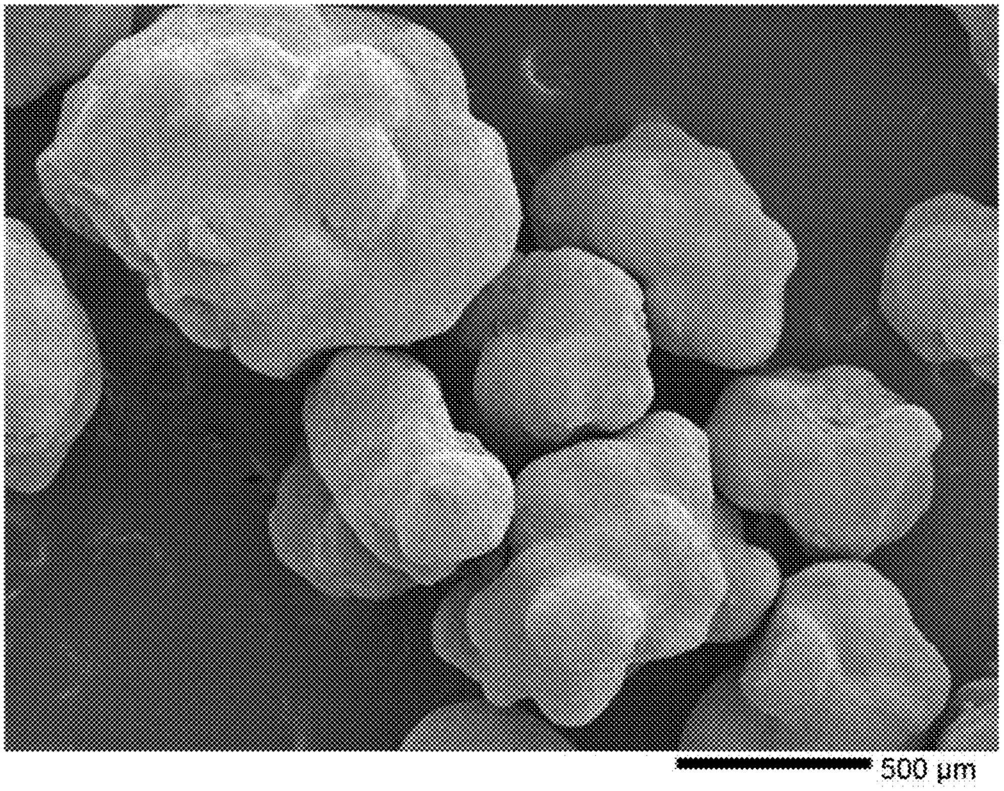
FIG. 3 shows a Scanning Electron Microscope image (50×) of the granulate of Example 3.

FIG. 3 shows a Scanning Electron Microscope image (50×) of the granulate.

Figure 4:
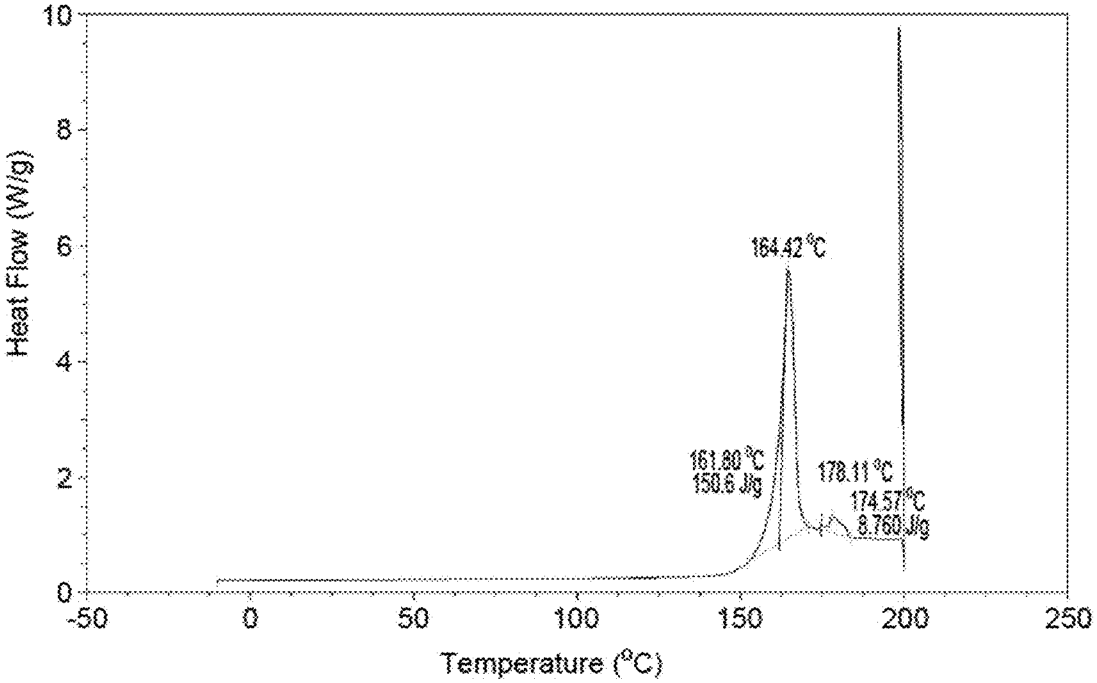
FIG. 4 shows the DSC curve so obtained by Example 3.

A sample of the granulate was analysed by means of DSC in the same way as in Example 2. The DSC so obtained is shown in FIG. 4. The moisture content and the DSC characteristics are shown in Table 3.

TABLE 3

| | |
|---|---|
| Moisture content (wt. %) | 0.50 |
| DSC characteristics | $T_{endo}$: 164.42° C., $T_{onset}$: 161.80° C., Enthalpy: 150.6 J/g |
| | $T_{endo}$: 178.11° C., $T_{onset}$: 174.57° C., Enthalpy: 8.760 J/g |

The upward shift of the endothermic peak to 164.42 °C (in comparison to the DSC curve of Example 2) is believed to be caused by the reduction of water content and the corresponding increase in crystalline co-crystal.

The particle size distribution of the granulates was determined using a Mastersizer 3000, Malvern:

Measurement: Dry dispersion

Analysis model: General purpose

Pressure: 0.5 bar

Dispersant Refractive Index: 1

Particle Absorption Index: 0

Particle Refractive Index: 1.53

The results of the particle size measurement are shown in Table 4.

TABLE 4

| $D_{10}$ (μm) | $D_{50}$ (μm) | $D_{90}$ (μm) | $D_{4,3}$ (μm) |
|---|---|---|---|
| 519 | 813 | 1321 | 876 |

Example 4

Moisture sorption of the granulate of Example 3 was determined at 20 °C and 40 °C. At 20 °C the maximum moisture uptake at RH 90% was 0.5 wt. %. At 40 °C the maximum moisture uptake at RH 90% was 1.2 wt. %.

Example 5

The hygroscopicity of a sample of the granulate of Example 3 was compared with that of a commercially available coated citric acid (ex Iwata Chemical Japan). It was found that when stored in an open cup at 30 °C, 75% RH for 1 month, the granulate did not pick up any water, whereas the coated citric acid picked up 8.4 wt. % of water Example 6

The sensory properties of the granulate of Example 3 were compared to those of a commercially available coated citric acid (ex Iwata and Capol) by using these powders in acid sanding with a 15:85 (w/w) blend of acid powder and sugar. The actual content of citric acid in the granulate is less compared to Capol coated citric but the sourness intensity has no significant difference. (See Table 6).

An attribute ranking sensory evaluation (scores from 1 to 9) was carried out in a session with 18 trained panellists. The results are summarised in Table 5.

TABLE 5

| | Citric acid content | Sourness intensity | Off-notes |
|---|---|---|---|
| Granulate | 7.5% | 8 | 4 |
| Coated citric acid Iwata | Not analyzed | 6 | 7 |
| Coated citric acid Capol | 14.6% | 9 | 5 |

Comparative Example

A glass bottle of 100 ml was charged with 21.00 g of citric acid monohydrate food grade (0.10 mol) and 7.56 g of glycine (0.10 mol). The powders were mixed by shaking the flask. Water (2.61 g) was added to the bottle, and the mixture was stored at 40 °C.

After two hours a clear viscous solution was formed, with a small amount of residual solids at the bottom of the flask. The next day a part of the product (10.35 g) was dried at room temperature under vacuum (p<10 mbara) for one night.

A foaming viscous syrup was formed, which was difficult to process and analyse.

The invention claimed is:

1. A co-crystal of citric acid and glycine, comprising citric acid and glycine in a molar ratio of 1:3.

2. The co-crystal according to claim 1, having an endothermic peak at a temperature of 130-200 °C and an enthalpy of at least 110 J/g, as determined by differential scanning calorimetry.

3. A particulate composition, comprising citric acid/glycine co-crystal particles having at least 5 wt. % of co-crystals, comprising citric acid and glycine in a molar ratio of 1:3.

4. The particulate composition according to claim 3, wherein the co-crystal particles comprise at least 50 wt. % of the co-crystals, comprising citric acid and glycine in a molar ratio of 1:3.

5. The particulate composition according to claim 3, wherein the particulate composition comprises at least 1 wt. % of the co-crystal particles.

6. The particulate composition according to claim 5, wherein the particulate composition comprises at least 90 wt. % of the co-crystal particles.

7. The particulate composition according to claim 5, wherein the particulate composition comprises 1-95 wt. % of the co-crystal particles and 5-99 wt. % of sugar particles.

8. The particulate composition according to claim 3, wherein the particulate composition has a volume weighted average diameter $D_{4,3}$ of 50-1,200 μm.

9. The particulate composition according to claim 3, wherein the particles of the particulate composition have the following particle size distribution:

$$D_{10} \geq 10\ \mu m;$$

$$50\ \mu m \leq D_{50} \leq 1{,}000\ \mu m;$$

$$D_{90} \leq 1{,}600\ \mu m;$$

wherein the vol. % of particles with diameters smaller than $D_x$ equals x vol. % and wherein the vol. % of particles with diameters larger than $D_x$ equals (100−x) vol. %.

10. The particulate composition according to claim 3, wherein the particulate composition has a water content of less than 5 wt. %.

11. A process of preparing co-crystal particles comprising co-crystal of citric acid and glycine, the process comprising:

(a) providing seed crystal particles containing at least 50 wt. % of crystalline material comprising an organic acid selected from citric acid, malic acid, lactic acid, acetic acid, fumaric acid, adipic acid, tartaric acid and combinations thereof;

(b) providing an aqueous solution containing citric acid and glycine in a molar ratio of 0.25 to 0.40;

(c) spraying the aqueous solution onto the seed crystal particles to produce loaded particles;

(d) removing water from the loaded particles.

12. A method of preparing an edible product, the method comprising combining a particulate composition according to claim 3 with one or more other food ingredients.

13. An edible product comprising at least 0.05 wt. % of co-crystal particles having at least 5 wt. % of a co-crystal according to claim 1.

14. The edible product according to claim 13, wherein the edible product is a confectionery product.

* * * * *